United States Patent [19]

Lang, Jr. et al.

[11] 4,131,676

[45] Dec. 26, 1978

[54] 2,6-BIS(1-MORPHOLINOALK-YLIDENEAMINO)ANTHRAQUINONES AS ANTI-AMEBIC AGENTS

[75] Inventors: Stanley A. Lang, Jr., Stoney Point; Paul F. Fabio, Pearl River; Yang-I Lin, Nanuet; Keith C Murdock; Thomas L. Fields, both of Pear River, all of N.Y.

[73] Assignee: American Cyanamid Company, Stamford, Conn.

[21] Appl. No.: 875,481

[22] Filed: Feb. 6, 1978

Related U.S. Application Data

[60] Continuation of Ser. No. 771,880, Feb. 25, 1977, abandoned, which is a continuation-in-part of Ser. No. 699,816, Jun. 24, 1976, abandoned, which is a division of Ser. No. 606,805, Aug. 22, 1975, abandoned.

[51] Int. Cl.$^2$ .................. C07D 295/00; A61K 31/535
[52] U.S. Cl. ................................ 424/248.56; 542/415; 544/79

[58] Field of Search ................... 542/415; 424/248.56; 544/79

[56] References Cited

U.S. PATENT DOCUMENTS

| 3,123,605 | 3/1964 | Turetsky et al. ................ 260/378 X |
| 3,184,482 | 5/1965 | Steiger .................................... 260/378 |
| 3,326,750 | 6/1967 | Weidinger ....................... 424/248.56 |
| 3,467,483 | 9/1969 | Bugaut et al. ......................... 260/378 |
| 3,478,064 | 11/1969 | Soladar et al. ....................... 260/378 |
| 3,654,319 | 4/1972 | Neeff ............................... 260/378 X |

FOREIGN PATENT DOCUMENTS

2521357  11/1976  Fed. Rep. of Germany.

*Primary Examiner*—Allen B. Curtis
*Attorney, Agent, or Firm*—Claude J. Caroli

[57] ABSTRACT

2,6-bis(-morpholinoalkylideneamino)anthraquinones that are effective against cecal and hepatic amebic infestations in warm-blooded animals are disclosed.

6 Claims, No Drawings

2,6-BIS(1-MORPHOLINOALK-YLIDENEAMINO)ANTHRAQUINONES AS ANTI-AMEBIC AGENTS

CROSS REFERENCE TO RELATED APPLICATIONS

This application is a continuation of application, Ser. No. 771,880 filed Feb. 25, 1977, now abandoned, which is a continuation-in-part of our co-pending application Ser. No. 699,816 filed June 24, 1976, now abandoned which, in turn, was a divisional application of Ser. No. 606,805 filed Aug. 22, 1975; and now abandoned.

DESCRIPTION OF THE PRIOR ART

U.S. Pat. No. 3,184,482 discloses a compound of the formula:

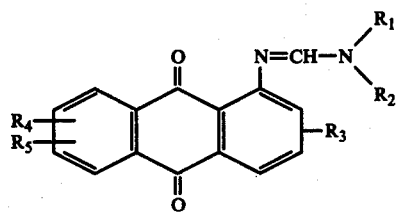

wherein $R_1$ and $R_2$ are hydrogen or lower alkyl and $R_3$, $R_4$, and $R_5$ are hydrogen, hydroxy or

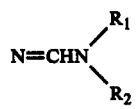

Utility is described as antibacterial antiviral, antiprotozoal and anthelmintic.

U.S. Pat. No. 3,654,319, Neeff, makes a gratuitous disclosure of a compound of the formula:

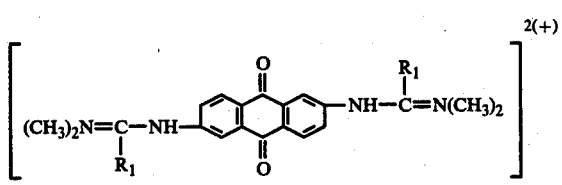

but the compound is neither claimed nor exemplified. Neeff does exemplify 1,4- and 1,5-diaminoanthraquinones of the following formulae:

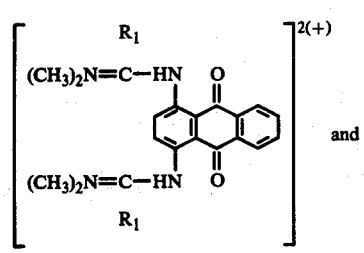

and

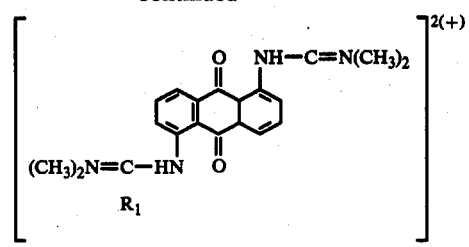

but applicants have prepared these compounds and have found them to be inactive for the claimed utility.

BRIEF SUMMARY OF THE INVENTION

This invention is concerned with novel compounds of the formula:

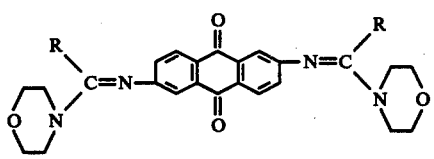

wherein R is selected from the group consisting of hydrogen and lower alkyl ($C_1$-$C_4$) and pharmaceutically acceptable salts thereof. This invention is also concerned with the method of treating cecal and hepatic amebic infections in warm-blooded animals with the disclosed compounds.

DETAILED DESCRIPTION OF THE INVENTION

The compounds of the present invention are normally crystalline solids being soluble in dimethylformamide and dimethylsulfoxide and less soluble in chloroform, alcohol and acetone. The salts (mono and di) are readily soluble in water and less soluble in alcohol.

The compounds of the present invention may be prepared according to the following methods:

(A) 2,6-Diaminoanthraquinone (1 mole) is reacted with a complex formed from phosphorous oxychloride (1.5 to 3 moles) and an N-acylmorpholine (2 to 6 or more moles) in a solvent such as acetonitrile (at a ratio of about 1-3 liters of solvent per mole of amine) at a temperature of 25° to 70° C for a period of about 1 to 24 hours.

More specifically, to a solution of the N-acylmorpholine in the solvent is added phosphorous oxychloride at −5° to 20° C. The resulting mixture is stirred at 0° to room temperature for 30 minutes to 6 hours. The 2,6-diaminoanthraquinone is added and the reaction mixture is stirred at 25° to 70° C for 1 to 24 hours. The reaction mixture is then poured into ice water and basified. The resulting crystals are collected by filtration and recyrstallized from an appropriate solvent or mixture of solvents such as chloroform/hexane.

(B) 2,6-Diaminoanthraquinone (72 parts) is slurried in 300 parts of a triethyl ortho acid and 250 parts of acetic anhydride is added. The mixture is refluxed for 1 to 8 hours, cooled and the solid product is collected, washed and dried. Purification is accomplished by dissolving this crude product in 1000 parts of chloroform, filtration and concentration of the filtrate. Further purification may be realized by recrystallization from a solvent such as dimethylformamide. A bis-imino-ether (8 parts)

is slurried in 45 parts of an appropriate amine. One equivalent of glacial acetic acid for each part of iminoether is added and the slurry is heated in an oil bath at 100°–160° C for 8 to 24 hours. (The use of a bomb is recommended with low boiling amines.) The reaction mixture is cooled. Products which crystallize are collected and recrystallized from a solvent such as methanol, ethanol, methyl cellosolve or dimethylformamide. For products which do not crystallize, the volatiles are removed in vacuo and the residue is dissolved in methanol. Upon cooling the product crystallizes and is recrystallized from a suitable solvent as above.

(D) Diethyl N,N'-(2,6-anthraquinonylene) di-formimidate is combined with at least 2 molar equivalents of a morpholine and heated at a temperature of 130°–200° C for 2 to 18 hours. The reaction mixture is stripped of volatiles under reduced pressure and the pure product is obtained by recrystallization from a suitable solvent.

The compounds of the present invention are active in treating cecal and hepatic amebic infections in warm blooded animals. Two tests which establish this activity are as follows:

ORGANISM

The organism used in both tests is the National Institute of Health 200μ strain of *Entamoeba histolytica*. This strain and an unidentified fecal flora are cultured in Cleveland-Collier Medium at 37° C. This medium consists of a liver infusion agar base overlaid with a horse serum:saline mixture (1:6) to which is added a few milligrams of sterile rice powder. The amebas are transferred to fresh medium twice weekly.

CECEL INFECTIONS IN FEMALE ALBINO WISTAR RATS

Pooled overlay (0.25 ml) containing large numbers of amebas is injected into the cecums of anesthetized weanling rats during laparotomy. Treatment is begun on the day after inoculation. The compounds are dissolved or suspended in 0.2% aqueous agar and administered once daily, by gavage, for 5 consecutive days. Six days after inoculation of the amebas, the rats are sacrificed and a scraping from the cecal wall of each rat is mixed with a drop of 0.85% saline and examined microscopically for amebas. A rat is considered cured if no amebas are seen. The cure or clearance rate (number cured/number treated) for each regimen is calculated and corrected for non-specific cures observed in the untreated infected controls. An active dose is the lowest dose, in terms of mg/kg/day, which clears or cures 50% of more of the rats so treated. The results of typical compounds of the present invention appear in the following table together with results obtained using known effective drugs for comparison.

HEPATIC INFECTIONS IN FEMALE GOLDEN HAMSTERS

A piece of ameba-laden absorbable sponge, about 25 millimeters square, is inserted between the middle lobes of the livers of anesthetized hamsters during laparotomy. Untreated hamsters usually die from the resulting infection about 7 days after inoculation. Treatment is started on the day of inoculation as soon as the hamsters recover from the surgical anesthetic. The test compounds are dissolved or suspended in 0.2% aqueous agar and administered once daily, by gavage, for 5 consecutive days. Effective regimens prevent mortality. Survival rates are corrected for non-specific survival observed in untreated groups. An active dose is the lowest dose, expressed in mg/kg/day, which protects 50% or more of the hamsters so treated as evidenced by survival 14 days after inoculation. The results of typical compounds of the present invention appear in the following table together with the active dose of known effective drugs for comparison.

TABLE

| COMPOUNDS | CECAL INFECTION Lowest Active Dose mg/Kg/day | HEPATIC INFECTION Lowest Active Dose mg/Kg/day |
|---|---|---|
| 2,6-bis(1-morpholinoethylideneamino)-anthraquinone | 50 | 100 |
| 2,6-bis(1-morpholinopropylideneamino)-anthraquinone | 100 | 100 |
| 6-n-Propyloxy-3-nitroimidazo 1,2-b-pyridazine | 20 | 25 |
| 2-Methyl-5-nitroimidazole-1-ethanol | 10 | 10 |
| Nitrimidazine | 20 | 100 |
| Tinedazole | 5 | 25 |

The novel 2,6-bis (1-morpholinoalkylideneamino)anthraquinones of the present invention are useful for ameliorating cecal and hepatic amebic infections in warm-blooded animals when administered in amounts ranging from about 0.5 mg. per kg. to about 40 mg. per kg. of body weight per day. A preferred dosage regimen for optimum results would be from about 2 mg. per kg. to about 29 mg. per kg. Thus, the daily dosage employed for a subject of about 70 kg. of body weight is about 35 mg. to about 2.8 g., and preferably about 140 mg. to about 2.0 g.

Suitable oral preparations consist, for example, of capsules, tablets, troches, suspensions, syrups and the like. In the case of tablets the principal active ingredient is mixed with conventional ingredients such as corn starch, lactose, sucrose, sorbitol, talc, stearic acid, magnesium stearate, dicalcium phosphate, gums or similar materials as nontoxic pharmaceutically acceptable diluents or carriers.

Sustained release formulations are also contemplated by the present invention.

The liquid forms in which the novel compositions of the present invention may be incorporated for administration include suitably flavored emulsions with edible oils, such as, cottonseed oil, sesame oil, coconut oil, peanut oil and the like, as well as elixirs and similar pharmaceutical vehicles. Sterile suspensions or solutions can be prepared for parenteral use. Isotonic preparations containing suitable preservatives are also desirable for injectable use.

EXAMPLE 1

N,N'-(2,6-Anthraquinonylene)-di-formimidic acid diethyl ester

A 35.7 g portion of 2,6-diaminoanthraquinone is mixed with 100 ml of triethylorthoformate containing 5 drops of concentrated $H_2SO_4$. The mixture is heated to reflux and the alcohol is removed as it forms over a 2 hour period. The reaction mixture is cooled to $-10°$ C, the solid which forms is collected by filtration, washed with 2B alcohol and air dried. Recrystallization from dimethylformamide produces brown crystals, mp 235°–250° C.

EXAMPLE 2

N,N'-2,6-Anthraquinonylenedi-propionimidic acid diethyl ester

A mixture of 7.2 g of 2,6-diaminoanthraquinone, 30 ml of triethylortho propionate and 25 ml of acetic anhydride is refluxed for 2 hours. The mixture is cooled to room temperature and a solid is collected by filtration then is washed with diethyl ester and dried in vacuo. The product is recrystallized from dimethyl formamide to give orange crystals, mp 195°–198° C.

EXAMPLE 3

2,6-Bis[(1-morpholinoethylidene)amino]anthraquinone

A 72 g portion of 2,6-diaminoanthraquinone

A 72 g portion of 2,6-diaminoanthraquinone, 300 ml of triethylorthoacetate and 250 ml of acetic anhydride are refluxed for 3 hours, cooled in an ice bath and the resulting brownish crystals are collected by filtration, washed with ether and dried giving N,N'-2,6-anthraquinonylenedi-acetimidic acid diethyl ester.

A 7.56 g portion of this imino ether and 40 ml of morpholine are heated in an oil bath at 135° C with a reflux condenser for 18 hours. The mixture is cooled in an ice bath. The brownish crystals are collected by filtration, washed with ether and dried in vacuo. These crystals are slurried in 100 ml of dimethylformamide, heated to boiling and filtered. The filtrate is stirred in a refrigerator for 3 hours and the yellow-orange crystals are collected by filtration and dried in vacuo, mp 285°–288° C.

EXAMPLE 4

2,6-Bis[(1-morpholinopropylidene)amino]anthraquinone

A mixture of 8.12 g of N,N'-2,6-anthraquinonylenedi-propionimidic acid diethyl ester (Example 17) and 40 ml of morpholine are heated in an oil bath with a reflux condenser at 130° C for 18 hours. The mixture is then cooled in an ice bath and the dark yellow solid is collected by filtration, washed with ether and dried in vacuo at 80° C, mp 220°–223° C.

We claim:

1. A compound of the formula:

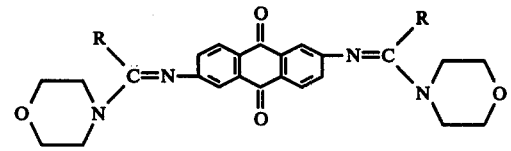

wherein R is selected from the group consisting of hydrogen and lower alkyl ($C_1$–$C_2$) and pharmaceutically acceptable salts thereof.

2. The compound according to claim 1, 2,6-bis[(1-morpholinoethylidene)amino]anthraquinone.

3. The compound according to claim 1, 2,6-bis[(1-morpholinopropylidene)amino]anthraquinone.

4. A method of treating cecal and hepatic amebic infections in warm-blooded animals which comprises administering to said animals an effective amount of a compound of the formula:

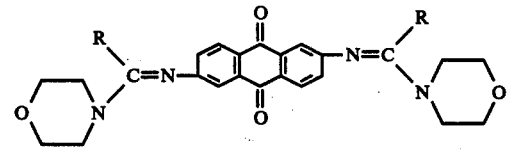

wherein $R_n$ is selected from the group consisting of hydrogen and lower alkyl ($C_1$–$C_2$) and pharmaceutically acceptable salts thereof.

5. The method according to claim 4 wherein the compounds is 2,6-bis[(1-morpholinoethylidene)amino]anthraquinone.

6. The method according to claim 4 wherein the compound is 2,6-bis[(1-morpholinopropylidene)amino]anthraquinone.

* * * * *